United States Patent [19]

Lecomte

[11] 4,441,078

[45] Apr. 3, 1984

[54] EDDY CURRENT APPARATUS INCLUDING A PROBE ARM PIVOTED FOR MOVEMENT BY CENTRIFUGAL FORCE FOR DETECTING FAULTS IN A METAL PLATE

[75] Inventor: Jean-Claude Lecomte, Buxy, France

[73] Assignee: Framatome, Courbevoie, France

[21] Appl. No.: 182,410

[22] Filed: Aug. 26, 1980

[51] Int. Cl.³ .......................................... G01N 27/90
[52] U.S. Cl. ..................................... 324/219; 324/262
[58] Field of Search ............................ 324/219–221, 324/346, 262; 73/40.5 R, 40.5 A

[56] References Cited

U.S. PATENT DOCUMENTS

| | | | |
|---|---|---|---|
| 2,684,464 | 7/1954 | Hastings et al. | 324/220 |
| 3,035,353 | 5/1962 | Hovemeyer et al. | 324/219 X |
| 3,529,236 | 9/1970 | Proctor | 324/220 X |
| 3,593,122 | 7/1971 | Barton et al. | 324/220 |
| 3,831,084 | 8/1974 | Scalese et al. | 324/219 X |
| 3,835,374 | 9/1974 | Frost | 324/220 |
| 4,105,972 | 8/1978 | Smith | 324/220 |
| 4,285,242 | 8/1981 | Braithwaite | 324/220 X |
| 4,304,134 | 12/1981 | Rouse et al. | 324/220 X |

FOREIGN PATENT DOCUMENTS 643794  1/1979  U.S.S.R. ........................... 324/219

Primary Examiner—Gerard R. Strecker
Attorney, Agent, or Firm—Pollock, Vande Sande & Priddy

[57] ABSTRACT

Apparatus and method for detecting, by means of eddy currents, faults in a metal plate with at least one bore, comprising a differential probe constituted by two coils connected electrically to an apparatus for producing and processing signals and an apparatus for moving the probe in the bore in translation and in rotation. The probe is constituted by a probe body in which a movable element is mounted, supporting the two coils and capable of moving under the action of centrifugal force so as to be applied to the inner wall of a tube inserted in the bore. The invention particularly applies to the testing of a steam generator tube sheet.

3 Claims, 2 Drawing Figures

EDDY CURRENT APPARATUS INCLUDING A PROBE ARM PIVOTED FOR MOVEMENT BY CENTRIFUGAL FORCE FOR DETECTING FAULTS IN A METAL PLATE

BACKGROUND OF THE INVENTION

1. Field of the Invention

The invention concerns the use of eddy currents for testing a metal plate, in particular a metal plate with borings.

It is especially intended to be applied to testing of a steam generator tube sheet.

2. Prior Art

Eddy currents have already been used for testing steam generator tubes. These are tested on site with internal probes by means of eddy currents, at the time of the initial complete inspection of boilers and on subsequent inspections in service. The test is entirely automated, which minimizes the exposure of personnel to ionizing radiation. A robot allows positioning of the probe at the inlet of each tube in the tube sheet, introduction of the probe in the tubes, extraction of the probe at a constant speed and obtaining of data on graphic recorder charts or magnetic tape. To introduce the probe in the tubes, a selective positioning apparatus is used, such as that described in French Patent Application No. 74-39771 in the name of applicant.

Though testing of steam generator tubes is possible with a certain number of known methods, in particular by use of eddy currents, a method of testing a region located beyond the tubes, namely the tube sheet, has not existed to date.

In addition, the methods used to detect faults in tubes have been mostly directed towards detecting longitudinal fissures, extending along the axis of the tube. They do not detect transverse fissures.

SUMMARY OF THE INVENTION

The present invention is an attempt to meet these requirements. It concerns an apparatus for detecting, by means of eddy currents, transverse faults in a metal plate with at least one bore in which a tube can be fitted, this detector apparatus comprising:

(a) a differential probe constituted by two coils whose axes are located in planes parallel to the plane of the plate and which are connected electrically to an apparatus for producing and processing signals, and (b) an apparatus for moving the probe in the bore in translation along the axis of the bore and in rotation about the latter, constituted by a transmission shaft connected on the one hand to driving members outside the bore.

According to the invention, the probe is constituted by a probe body in which a movable element is mounted supporting the two coils and capable of moving under the action of centrifugal force so as to be applied against the inner wall of a tube fitted in the bore. A constant spacing is thus maintained between the probe and the walls of the bore.

In a particular embodiment of the invention, the movable element is constituted by a lever arm at the end of which the two coils are mounted. This lever arm is articulated to the probe body about a single axis or preferably about two axes perpendicular to each other, these axes being parallel to the plane of the plate.

To add to the action of centrifugal force, which allows a constant spacing to be maintained between the probe and the walls of the bore, the probe can be provided with a spring for spacing the movable element with respect to the probe body.

In a preferred embodiment of the invention, the apparatus for processing signals has a programmable filter whose control unit is slaved to the rate of rotation of the probe.

An automatic selective positioning apparatus is preferably used to set the probe in position.

A further object of the invention is a method of detecting, by means of eddy currents, faults in a metal plate with at least one bore, using an apparatus according to the invention.

BRIEF DESCRIPTION OF THE DRAWINGS

The invention will now be described in more detail with more particular reference to two embodiments given as examples and represented by the attached drawings.

The corresponding elements in the two figures have the same reference numerals.

DESCRIPTION OF THE PREFERRED EMBODIMENTS

Figure 1:
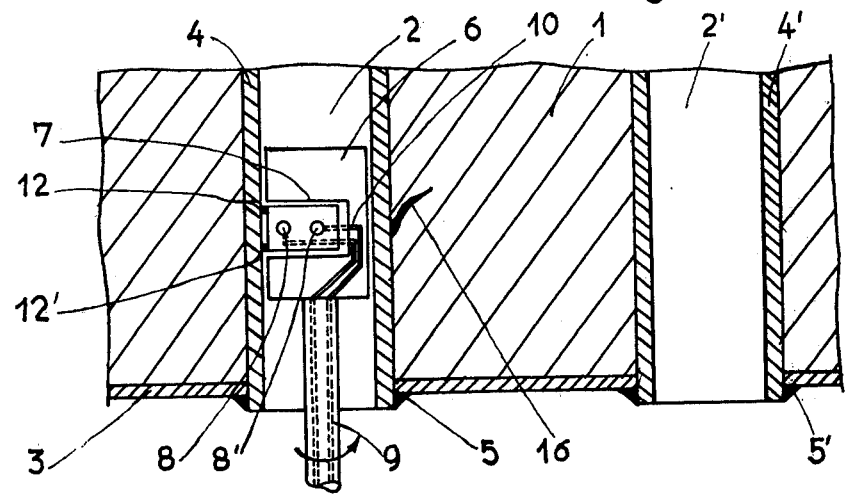
FIG. 1 represents, in section, a metal plate which has bores and which has in one of the bores a simple apparatus embodying the invention.

Reference 1 indicates a metal plate which may, for example, be the tube sheet of a steam generator in a pressurized water nuclear power station, of the type disclosed in French Patent Application No. 74-39771 filed by the applicant.

Plate 1 has bores 2 and 2'. The plate 1 is covered with a layer 3 of Inconel, and Inconel tubes 4 and 4' are inserted in the bores 2 and 2', welded at points 5 and 5' and then beaded. The tubes 4 and 4' are represented as emerging from the bore 2, but they could also be recessed.

The faults to be detected may be fissures or the beginnings of fissures opening at or near the bore 2, these fissures being radial with respect to the axis of the tube 4. The faults to be detected may also be separation of the plate 1 and the Inconel covering 3, opening into the bore 2 or in its proximity.

More particular reference will now be made in FIG. 1.

In this figure, the probe is constituted by a probe body 6 acting as centering device in which a movable element 7 is mounted, supporting two coils 8 and 8', each surrounding a ferrite.

A transmission shaft 9 connected on the one hand to the probe and on the other hand to driving members (not shown) constitutes the apparatus for moving the probe in translation along the axis of the tube 4 and in rotation about this axis. One skilled in the art will have no difficulty in selecting suitable driving members, such as a screw and nut system.

The two coils 8 and 8' are electrically connected by means of connections 10, allowing movement of the coils, to an apparatus for producing and processing signals, as regularly used in apparatuses for detection by eddy currents. The connection cables pass through the interior of the shaft 9.

The movable element 7 moves under the action of the centrifugal force resulting from the rotation of the shaft 9 and is applied against the inner wall of the tube 4. For this purpose, it is provided with wear pads 12 and 12' rubbing against the inner wall of the tube 4. The spacing between the probe and the walls of the bore is therefore kept constantly equal to the thickness of the tube 4.

Figure 2:
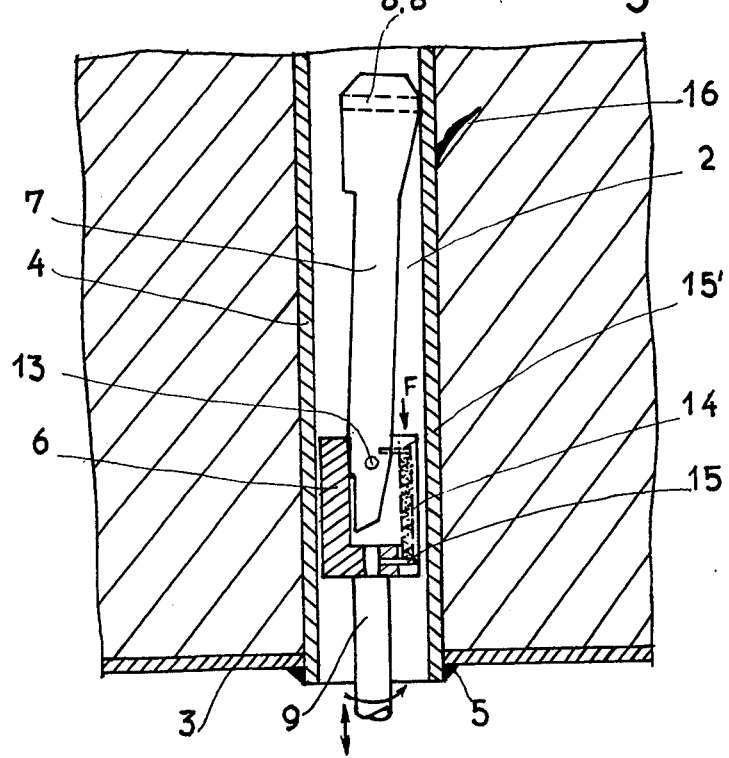
FIG. 2 represents, in section, a metal plate which has a bore and which is provided with a detector apparatus according to the invention in which the movable element of the probe is constituted by a lever arm articulated to the probe body about an axis parallel to the plane of the plate.

Reference will now be made to FIG. 2.

In this figure, the movable element 7 is constituted by a lever arm on which the two coils 8 and 8' are mounted. The lever arm 7 is pivotally articulated to the probe body 6 about an axis 13 parallel to the plane of the plate 1. (In a variant of embodiment, the arm 7 could be articulated about two axes perpendicular to each other: the probe would thus be given an additional degree of freedom).

The lever arm 7 moves under the action of the centrifugal force resulting from the rotation of the shaft 9 so that its end bearing the coils 8 and 8' is applied against the inner wall of the tube 4.

To add to the force exerted on the end of the lever arm, a spring 14 can be installed, attached on the one hand to the probe body 6, at one of its ends 15, and on the other hand to the lever arm 7 at its second end 15'. The spring 14 is stretched and exerts a force F on the lever arm 7, at the point 15, which causes the lever arm 7 to turn about its axis 13 of articulation and thus applies the part of the lever arm 7 bearing the coils 8 and 8' to the wall of the tube 4.

A spring such as 14 has not been represented in the embodiment of FIG. 1, but the addition of a spring which would add to the centrifugal force and if necessary allow the speed of rotation of the shaft 9 to be lessened could easily be envisaged in this embodiment also.

The coils have been represented in FIGS. 1 and 2 with parallel axes and located in the same plane of revolution. Such a probe, of the differential type, is used to detect faults such as the radial fissure 16 represented in FIGS. 1 and 2.

The coils of the probe could also be positioned in different planes; such a probe would then be used to detect faults in the adherence between the plate 1 and the covering 3, which open into or near the bore.

The different sorts of coil are intended to be interchangeable so that the two sorts of faults can be detected alternately and quickly.

As with testing of steam generator tubes, multifrequency eddy currents are used. In practice, a monofrequency apparatus cannot extract all the data contained in each signal.

The apparatus for producing and processing signals is the same as for testing tubes. It is located outside the steam generator, beyond the region of dangerous radioactivity. The signal processing chain comprises a programmable filter whose control unit is slaved to the rate of rotation of the probe. The results are all recorded on magnetic tape or paper recorder charts.

A selective positioning apparatus such as that described in French Patent Application No. 74-39771, preferably automatically controlled, is used to position the probe; the whole of the plate 1 can thus be tested by putting the probe successively in all the holes.

The invention is not limited strictly to the two embodiments described by way of example; it also covers embodiments which only differ in detail, variants or use of equivalent means.

Thus, closure of the magnetic circuit of the ferrites contained in the coils 8 and 8' so as to increase focussing of the sheet of currents and reduce losses can be envisaged.

I claim:

1. Apparatus for detecting, by means of eddy currents, faults (16) in a metal plate (1) having at least one bore (2), comprising
   (a) a differential probe comprising a probe body (6) having two ends, and two coils (8, 8') having their axes located in planes parallel to the plane of said plate (1) and electrically connected to an apparatus for producing and processing eddy current signals;
   (b) means for moving said probe in said bore (2) in translation along the axis of said bore (2) and in rotation about the latter, said means comprising a transmission shaft (9) connected to one end of said probe body inside said bore (2),
   (c) said probe body (6) including an arm (7) having a free end and a pivot end, said arm (7) extending from the other end of said probe body along the axis of said bore and being pivotally articulated to said probe body at its pivot end so as to be movable about an axis parallel to the plane of said plate, said arm (7) having said two coils (8, 8') mounted at its free end, the centrifugal force produced by the rotational movement transmitted to said probe, and consequently to said arm (7), causing said free end of said arm (7) to move against the inner wall of a tube (4) inserted in said bore (2).

2. Detector apparatus according to claim 1, wherein said arm (7) is articulated to said probe body (6) about two axes parallel to the plane of said plate (1) and perpendicular to each other.

3. Detector apparatus according to any one of claims 1 or 2, wherein said probe includes a spring (14) for spacing said movable element (7) with respect to said probe body (6).

* * * * *